United States Patent [19]

Reichenbacher et al.

[11] 3,935,234

[45] Jan. 27, 1976

[54] CHEMICAL CONDENSATION IMPROVEMENT

[75] Inventors: Paul H. Reichenbacher, Elk Grove Village; Theresa M. Forsythe, Mount Prospect; Allen K. Sparks, Des Plaines; Ted Symon, Lombard, all of Ill.

[73] Assignee: Universal Oil Products Company, Des Plaines, Ill.

[22] Filed: Aug. 2, 1973

[21] Appl. No.: 384,999

Related U.S. Application Data

[63] Continuation-in-part of Ser. No. 172,573, Aug. 17, 1971, abandoned.

[52] U.S. Cl..... 260/343.2 R; 260/521 R; 260/473 S
[51] Int. Cl.$^2$................C07D 311/06; C07C 69/76; C07C 65/02

[58] Field of Search....... 260/343.2 R, 521 R, 473 S

[56] References Cited
UNITED STATES PATENTS
3,803,175   4/1974   Sparks et al. .................... 260/343.2

*Primary Examiner*—John M. Ford
*Attorney, Agent, or Firm*—James R. Hoatson, Jr.; Raymond H. Nelson; William H. Page, II

[57] ABSTRACT

Metal-containing catalyst compounds which are soluble in reaction mediums are maintained in the desired soluble form during an alternate oxidation and reduction process by utilizing an inert solid material in the reaction mixture.

9 Claims, No Drawings

CHEMICAL CONDENSATION IMPROVEMENT

CROSS-REFERENCE TO RELATED APPLICATIONS

This application is a continuation-in-part of our copending application Ser. No. 172,573 which was filed Aug. 17, 1971, now abandoned.

BACKGROUND OF THE INVENTION

The prior art is replete with various solid supports or catalysts which are present in chemical reactions. However, all of these prior art references have in common the fact that the catalysts thereof are employed in a solid or slurry form, the solid material which is used being as a catalyst support or as a means for slurrying the catalyst. One particular prior art reference describes a solid support which is used specifically to adsorb and bind the reduced metallic non-oxidized insoluble solid catalysts, examples of these catalysts being solid palladium metal in a zero valence state composited on charcoal, solid nickel metal in a zero valence state composited on kieselguhr, etc., the efficacy of the process depending upon the maintenance of the metal-containing catalyst in certain reduced, insoluble, non-dissolved, solid, precipitated, dispersed forms. Using the reaction conditions set forth in this reference, the catalyst metal in the zero valence state will not dissolve, that is, it will not be a solute in the liquid reaction mixture. Furthermore any soluble metal which may be introduced into the system would be reduced to the metallic state. The solubilization of the metal from the catalysts disclosed in this reference by using an oxidizing atmosphere, as taught in the present application, would be detrimental to the methods set forth in this reference in view of the catalyst activity and economic losses which would occur due to metal solubilization.

In contradistinction to the prior art, it will be hereinafter shown in greater detail that it is possible to obtain improved yields of the desired products by effecting a condensation reaction in the presence of an oxygen-containing gas and a catalyst comprising a metal-containing compound which is soluble on the reaction medium in the presence of an inert solid material, the efficiency of the process of this invention depending upon the maintenance of the metal-containing compound in an oxidized, soluble, dissolved and non-solid form.

This invention relates to a method for the maintenance of catalytic compositions of matter in a desirable form. More specifically, the invention is concerned with a method for maintaining catalysts in a soluble form while effecting a chemical reaction in the presence of a catalyst comprising a metal-containing compound which is soluble in the reaction medium and an oxygen-containing gas, the maintenance of the metal-containing compound in soluble form being enhanced by the presence of an inert solid material.

A wide variety of chemical reactions, a particular example being a condensation reaction involving the use of an oxygen-containing gas, are catalyzed by compositions of matter comprising metal-containing compounds such as metal cations or metal complexes which are homogeneous in the reaction medium. Therefore, during the course of many of these reactions, the metal-containing catalytic compositions of matter are alternately reduced and oxidized. During this alternate reduction and oxidation, the metal-containing catalyst which is in a soluble, homogeneous state is sometimes reduced to a point where the metal is in a zero valence state and therefore may deposit out on the reactor walls or become powdery in nature. In each case, oxidation of the metal in a zero valence as a solid may not be efficient under the conditions of the reaction, and therefore the loss of the soluble metal catalyst reduces the rate of the reaction to a point which is not economically feasible to operate, or in extreme instances, will stop the reaction completely. This then necessitates replacement of the catalyst with additional amounts thereby reducing the efficiency of the reaction and increasing the cost of operation to a point, as hereinbefore set forth, may render the process economically unfeasible to operate.

It is therefore an object of this invention to provide a method for maintaining the catalyst system in a homogeneous state.

A further object of this invention is to provide a method whereby soluble metal-containing catalytic compositions of matter are maintained in said soluble form, thus permitting the reaction which employs the catalyst to proceed at an efficient rate of operation.

In one aspect an embodiment of this invention is found in a chemical condensation reaction in the presence of an oxygen-containing gas and a catalyst comprising a metal-containing compound which is soluble in the reaction medium, said chemical reaction being operated under conditions such that the metal component of said metal-containing compound is alternately reduced to a valence state of zero and oxidized back to the higher valence state of its soluble form, the improvement in the process comprising effecting said reaction in the presence of an inert solid material.

A specific embodiment of this invention is found in a palladium-containing catalyst in soluble form during a chemical condensation reaction which is effected in the presence of an oxygen-containing gas and said palladium-containing catalyst, said chemical reaction being operated under conditions such that the palladium component of said palladium-containing catalyst is alternately reduced to a valence state of zero and oxidized back to the higher valence state of its soluble form, the reaction being effected in the presence of γ-alumina.

Other objects and embodiments will be found in the following further detailed description of the present invention.

As hereinbefore set forth the present invention is concerned with a process or method for maintaining metal-containing catalysts in a predetermined physical stae and preferably in a soluble state. This is advantageous when utilizing a catalyst in the state in a variety of chemical reactions. As an illustration of the difficulty which may be encountered when utilizing a metal-containing catalyst, the following equations are set forth in which R is the reacting system, $R_{(ox)}$ is the product or products desired and $n$ is 1, 2 or 3 depending upon the valence of the metal portion of the catalyst.

$$R + M^{n+} \rightarrow R_{(ox)} + M^°$$
$$4M^° + 4nH^+ + nO_2 \rightarrow 4M^{n+} + 2nH_2O$$

As shown in the above reactions, it is possible that the metal-containing catalyst which is soluble in the reaction system is sometimes reduced to a metal layer which deposits on the reactor walls or to a metal powder. When this occurs, oxidation of these types of metals in a valence state of zero may not be efficient under the reaction conditions which are suitable for promoting the reaction set forth in the first equation. Thus, as hereinbefore set forth, there is a loss of the soluble metal catalyst which will retard the formation of the desired product, or in some instances, stop the reaction completely.

It has now been discovered that by effecting the reaction in the presence of an inert solid support, it will be possible to maintain the catalyst in the desired physical state, which, in many instatnces, is in solution, the presence of the support assisting in the oxidation of the metal in a valence state of zero back to the desired valence state and thus preventing the formation of metallic layer or powder, each of which is difficult to oxidize. By permitting the metal in a valence state of zero to form on the surface of the solid support, it will permit an efficient and rapid re-oxidation of the metal in a valence state of zero back to the desired higher valence state, thus allowing the metal to remain in a soluble state. In other words, the inert solid material assists the oxidation of the zero valence metal by providing a large surface area onto which the zero valence metal will adsorb, and, being so adsorbed, will itself have a larger surface area than it would have had if the inert solid material were not present. The adsorbed metal thereby achieves a higher surface-to-mass ratio than it would achieve by adsorption onto the reactor walls in the absence of the inert solid material. Therefore, the adsorbed zero valence high surface area metal is oxidized by the chemical oxidants present in the reaction system at a rate much faster than the rate of oxidation of an equivalent mass of non-adsorbed zero valence low surface area metal, precisely because of the high surface area of the former metal.

Examples of some of the catalysts which may be maintained in the soluble form comprise those transition metals which would ordinarily be reduced to a valence state of zero during reactions which they are used to catalyze. Particularly speaking, these metal-containing catalysts would include those metals of Groups VIII and IB of the Periodic Table, and specifically the salts of platinum, palladium, nickel, cobalt and silver. Illustrative examples of these salts would be platinum acetate, platinum acetylacetonate, platinum chloride, platinum bromide, palladium acetate, palladium acetylacetonate, palladium chloride, palladium bromide, nickel acetate, nickel acetylacetonate, nickel chloride, nickel bromide, cobalt acetate, cobalt acetylacetonante, cobalt chloride, cobalt bromide, silver acetate, silver acetylacetonate, silver chloride, silver bromide, etc. It is to be understood that the present invention is not necessarily limited to the maintenance of the above-mentioned catalysts in a soluble form but will extend to other catalyst salts which are soluble form and which may have the metal salts thereof reduced to zero during the specific reaction which they are employed.

The solid supports which may be utilized in the present invention comprise those which are inert or substantially inert and are not effected by the particular reaction in which they are employed. These solid supports may include both low surface area and high surface area compounds, the high surface area supports being preferred inasmuch as the metal which is deposited thereon may be more readily oxidized back to a higher valence state. Some specific examples of these solid supports will include carbon, activated carbon, diatomaceous earths such as kieselguhr, clays such as montmorillonite, kaolin, metal oxides and mixtures thereof such as alumina, either the alpha, gamma, eta, or theta variety, silica, silica-alumina, silica-magnesia-alumina, silica-alumina-magnesia, silica-alumina-zirconia, etc.

The solid support may be utilized to maintain the catalysts in a soluble state when effecting the particular reactions in either a batch or continuous type of operation. For example, when a batch type operation is used, the solid support is placed in an appropriate reaction apparatus which may comprise a flask or a pressure vessel such as an autoclave of the rotating or mixing type, the choice of said apparatus being dependent upon the particular reaction conditions which are to be employed during the reaction. Following this the catalyst is added to the reaction vessel, the feed stock is charged thereto and the reactor is sealed. In the preferred embodiment of the invention an oxygen-containing gas such as air or oxygen is also charged thereto and the reaction is allowed to proceed while employing a predetermined set of reaction conditions. These reaction conditions include elevated pressures as well as elevated temperatures, the reactor being heated to the desired operating temperature and the desired operating pressure is reached by utilizing the oxygen-containing gas such as air or oxygen. In the event that the oxygen-containinng gas is programmed to supply only a partial amount of the desired operating pressure, the remainder may be obtained by also charging thereto an inert gas such as nitrogen. The oxygen-containing gas is to be employed for the purpose of oxidizing the catalyst back to a higher valence state after said catalyst has had the metal portion thereof reduced to a valence state of zero. Upon completion of the desired residence time, the reactor is allowed to return to ambient temperature and any excess pressure is discharged to return the vessel to atmospheric pressure. The reaction mixture is recovered and the desired product is separated from any unreacted starting material and recovered by conventional means such as washing, drying, extraction, filtration, fractional distillation under reduced pressure, fractional crystallization, etc.

When employing a continuous manner of operation, the solid support of the type hereinbefore set forth in greater detail is placed in an appropriate apparatus which is maintained at the proper operating conditions of temperature and pressure. Following this the catalyst, oxygen-containing gas, and the feed stock are charged thereto through separate lines or, if so desired, the catalyst may be admixed with the feed stock and the resulting mixture charged thereto in a single stream. Upon completion of the desired residence time, the reactor effluent is continuously withdrawn and subjected to conventional means of separation whereby the desired product will be recovered and removed to storage, while any unreacted starting materials may be recycled to form a portion of the feed stock.

The following examples are given to illustrate the process of the present invention which, however, are not intended to limit the generally broad scope of the present invention in strict accordance therewith.

EXAMPLE I

To illustrate the operablility of the present invention, an experiment was performed in which 282 grams (3.0 moles) of phenol, 180 grams (3.0 moles) of acetic acid, 103 grams (1.20 moles) of methyl acrylate, 12.0 grams (0.0602 moles) of cupric acetate monohydrate, 0.70 grams (0.0031 mole) of palladium acetate along with 6 grams of a finely divided inert diatomaceous earth known in the trade as Celite were placed in a flask. Following this, air was bubbled into the solution at a rate of two cubic feet per hour, the reaction being effected at atmospheric pressure, and the contents of the flask wre heated to a temperature of 90°C. The reaction contined for a period of 7 hours with the subsequent formation of the methyl esters of o- and p-hydroxycinnamic acids and coumarin. During the entire reaction period, the catalyst remained in soluble form and did not precipitate out.

In contrast to this, when the same experiment was repeated, the significant difference being the Celite was not present in the reaction mixture, a black shiny metallic mirror of elemental palladium precipitated out and formed on the wall of the glass reactor.

EXAMPLE II

In another example, 282 grams (3.0 moles) of phenol, 182 grams (3.04 moles) of acetic acid, 52.0 grams (0.604 moles) of methyl acrylate, 2.4 grams (0.012 moles) of cupric acetate monohydrate, 1.4 grams (0.0062 moles) of pallidium acetate, and 6 grams of a finely divided inert diatomaceous earth known in the trade as Celite were placed in a stainless steel autoclave. The autoclave was sealed and pressured to 250 pounds per square inch with air; this pressure being maintained as the mixture was stirred and air was bubbled through it at a rate of two cubic feet per hour (measured at atmospheric pressure). The mixture was heated to 90°C. for 3.5 hours while maintaining the stirring and the air flow, hereinbefore described. The catalyst did not precipitate out on the walls of the autoclave, while the methyl esters of o- and p-hydroxycinnamic acids and coumarin were obtained in a good yield.

By way of contrast, when the same experiment was repeated, except that Celite was not present in the reaction mixture, a black, shiny mirror of elemental palladium formed on the inner walls of the autoclave, and black, powdery elemental palladium was formed. The yield of methyl esters of o- and p-hydroxycinnamic acids and coumarin was greatly reduced when compared to the yield of the methyl esters of o- and p-hydroxycinnamic acids utilizing the 6 grams of Celite in the reaction mixture.

EXAMPLE III

As a further illustration of the difference which exists when utilizing an inert solid material, 4.7 grams of a catalyst containing 6.79% (0.003 mole) of palladium adsorbed on a diatomaceous earth known in the trade as Hyflo Super-Cel Celite along with 6.0 grams (0.030 mole) of cupric acetate monohydrate and 66 grams (1.10 mole) of glacial acetic acid were placed in a 300 cc. stirred, stainless steel autoclave. The autoclave was sealed and air was pressed in until an initial operating pressure of 1400 pounds per square inch gauge was reached. The autoclave was heated to a temperature of 100°C. and stirred for a period of 4 hours. At the end of this period, the autoclave and contents thereof were allowed to return to room temperature, the excess pressure was vented and the recovered solid was subjected to chemical analysis. It was found that the solid contained only 0.31% of palladium metal. Thus, 95% of the palladium had been oxidized and dissolved into the acetic acid, the catalyst thus being maintained in a soluble form.

EXAMPLE IV

In contradistinction to the experiment performed to Example III above, another experiment was performed in which a mixture comprising 0.213 grams (0.002 mole) of palladium black powder, 4.0 grams (0.020 mole) of cupric acetate monohydrate and 44 grams (0.73 mole) of glacial acetic acid was placed in a 300 cc. stirred, stainless steel autoclave. The autoclave was sealed and air was again pressed in until an inital operating pressure of 1400 pounds per square inch gauge was reached. Thereafter the autoclave was heated to a temperature of 100°C. and stirred for a period of 4 hours while maintaining the autoclave at this temperature and pressure. At the end of the 4-hour period, heating was discontinued, the autoclave and contents thereof were cooled to room temperature, the excess pressure was vented, there being found that only 0.0626 grams of palladium, amounting to 29% of the palladium powder charged, was found to be dissolved in the acetic acid. It is therefore strikingly illustrated by a comparison of the results obtained in Examples III and IV that the presence of a solid material in the reaction zone will assist in the oxidation of the catalyst in zero valence state and will thus permit the catalyst to remain in the desired form, namely, a soluble, oxidized state.

EXAMPLE V

As a further illustration of the ability of a catalyst which is maintained in a soluble, non-solid, oxidized stated to convert the reactants into a relatively high yield of the desired product, a mixture comprising 0.5 mole of benzene, 0.10 mole of methyl acrylate, 0.50 mole of glacial acetic acid, 0.002 mole of palladium (II) acetylacetonate and 0.002 mole of cupric acetate monohydrate was charged to a 300 cc. stirred, stainless steel autoclave. The autoclave was sealed and air was pressed in until an initial operating pressure of 1100 pounds per square inch gauge was reached. The autoclave was stirred, heated to a temperature of 120°C. and maintained at the aforementioned operating temperature and pressure for a period of 6 hours. During this time the bulk of the palladium and copper salt remained dissolved in the reaction medium. During the 6-hour reaction time, liquid samples were periodically withdrawn and analyzed by means of gas chromatography. At the end of the 6-hour period, an 86% conversion of the methyl acrylate and a 70% yield of methyl cinnamate, the desired product, based on the methyl acrylate charged, were noted.

EXAMPLE VI

In contradistinction to the above experiment, another experiment was run utilizing a solid catalyst. To a 300 cc. stirred, stainless steel autoclave was added 0.5 mole of benzene, 0.10 mole of methyl acrylate, 0.50 mole of glacial acetic acid, 0.002 mole of cupric acetate monohydrate and 0.002 mole of palladium black powder. The latter comprised a solid catalyst and was used in place of the palladium (II) acetylacetonate which was the soluble catalyst in the above experiment. The autoclave was sealed and pressured to 1500 pounds per square inch gauge with air. Thereafter the autoclave was stirred, heated to a temperature of 120°C. and maintained thereat for a period of 6 hours.

During this reaction period, the bulk of the palladium powder remained in solid form and did not dissolve in the reaction medium. As in the above example, liquid samples were again periodically withrawn during the reaction time and analyzed by means of gas chromatography. After 6 hours of reaction, it was noted that there had been only a 10% conversion of the methyl acrylate and only a 10% yield of methyl cinnamate, the desired product, based on the methyl acrylate charged.

It is therefore readily apparent from a comparison of the above examples that there is a substantial difference in activity between a solid catalyst and a catalyst which is soluble in the reaction mixture, the latter catalyst being effective in obtaining a yield which is seven times greater and a conversion which is over eight times greater than that which is obtained when utilizing a solid catalyst which does not dissolve in the reaction mixture.

By utilizing the process of the present invention in which an inert solid material of the type hereinbefore set forth in greater detail is present in the reaction mixture to assist in maintaining the metals in soluble, oxidized form rather than in a solid form during the alternate oxidation and reduction of the metal, it is possible to obtain a greater yield of the desired product than that which is obtained when omitting the presence of the inert solid material.

EXAMPLE VII

In this example, a mixture of 3 moles of phenol, 3 moles of acetic acid, 0.5 mole of methyl acrylate, 0.06 jmole of cupric acetate, 0.00624 mole of palladium acetylacetonate and 6 grams of γ-alumina is placed in a glass reactor. Following this, air is bubbled into the mixture with continuous stirring and the mixture is heated to a temperature of 90°C. for a period of 7.5 hours. At the end of the aforementioned reaction time, heating is discontinued and the reaction mixture is recovered. The desired product comprising the methyl esters of o- and p-hydroxycinnamic acids is recovered in a relatively high yield, the catalyst comprising palladium acetylacetonate remaining in a soluble form without depositing any elemental palladium on the walls of the reactor. In contrast to this, when the above experiment is repeated omitting the γ-alumina in the reaction mixture, it will be found that the palladium acetylacetonate is reduced and palladium in a valence state of zero will deposit out on the walls of the reactor.

EXAMPLE VIII

A mixture of equimolar amounts of phenol and acetic acid along with acrylic acid, cupric acetate, platinum acetate, and activated carbon is treated in a manner similar to that hereinbefore set forth in Examples I to VII. Upon completion of the desired residence time of 7.5 hours, during which time the mixture is continuously stirred while being heated to a temperature of 90°C., and air being introduced at a rate of two cubic feet per hour, the reaction mixture is recovered. It will be found that coumarin is produced in a relatively good yield without any loss of the platinum acetate catalyst, there being no deposit of elemental platinum on the walls of the reactor.

As in the previous examples, when the experiment is repeated in the absence of any activated carbon, there will be a lower yield of coumarin produced with an attendant deposition of elemental platinum in a valence state of zero on the walls of the reactor.

We claim as our invention:

1. In the chemical condensation of phenol or benzene with acrylic acid or its methyl ester in the presence of an oxygen-containing gas and a compound of a noble metal of Group VIII of the Periodic Table which is soluble in the reaction medium, said chemical reaction being operated under conditions such that the metal component of said metal-containing compound is alternately reduced to a valence state of zero and oxidized back to the higher valence state of its soluble form, the improvement which comprises effecting said reaction in the presence of an inert high surface area solid material selected from the group consisting of carbon, activated carbon, diatomaceous earth, clay and metal oxides.

2. The process as set forth in claim 1 in which said inert solid material is a high surface area alumina.

3. The process as set forth in claim 2 in which said high surface area is alumina is γ-alumina.

4. The process as set forth in claim 1 in which said inert solid material is a diatomaceous earth.

5. The process as set forth in claim 1 in which said inert solid material is activated carbon.

6. The process as set forth in claim 1 in which said inert solid material is silica-alumina.

7. The process as set forth in claim 1 in which said inert solid material is a clay.

8. The process as set forth in claim 1 in which said noble metal is palladium.

9. The process as set forth in claim 1 in which said noble metal is platinum.

* * * * *